US012186507B2

(12) United States Patent
Kojima et al.

(10) Patent No.: US 12,186,507 B2
(45) Date of Patent: Jan. 7, 2025

(54) BALLOON FOR BALLOON CATHETER AND METHOD FOR MANUFACTURING BALLOON CATHETER

(71) Applicant: KANEKA CORPORATION, Osaka (JP)

(72) Inventors: Masahiro Kojima, Settsu (JP); Yoshinori Nakano, Settsu (JP); Yojiro Koga, Settsu (JP); Masato Tsueda, Settsu (JP); Shintaro Osumi, Settsu (JP)

(73) Assignee: KANEKA CORPORATION, Osaka (JP)

( * ) Notice: Subject to any disclaimer, the term of this patent is extended or adjusted under 35 U.S.C. 154(b) by 433 days.

(21) Appl. No.: 17/615,663

(22) PCT Filed: May 12, 2020

(86) PCT No.: PCT/JP2020/018980
§ 371 (c)(1),
(2) Date: Dec. 1, 2021

(87) PCT Pub. No.: WO2020/250611
PCT Pub. Date: Dec. 17, 2020

(65) Prior Publication Data
US 2022/0218960 A1    Jul. 14, 2022

(30) Foreign Application Priority Data
Jun. 11, 2019 (JP) .................................. 2019-108432

(51) Int. Cl.
*A61M 25/10*    (2013.01)
*B29C 49/48*    (2006.01)

(52) U.S. Cl.
CPC ...... *A61M 25/1002* (2013.01); *A61M 25/104* (2013.01); *A61M 2025/1031* (2013.01); *A61M 2025/1086* (2013.01)

(58) Field of Classification Search
CPC ........ A61M 2025/1086; A61M 25/104; A61M 25/1002; B29C 2049/4882; B29L 2031/7543
See application file for complete search history.

(56) References Cited

U.S. PATENT DOCUMENTS 9,302,079 B2 *    4/2016    Burton .............. A61M 25/1029
2003/0055378 A1    3/2003    Wang et al.
(Continued)

FOREIGN PATENT DOCUMENTS

EP    2 942 079 A1    11/2015
JP    7-289559 A    11/1995
(Continued)

OTHER PUBLICATIONS

Extended European Search Report for European Application No. 20822806.4, dated Jun. 22, 2023.
(Continued)

*Primary Examiner* — Robert B Davis
(74) *Attorney, Agent, or Firm* — Birch, Stewart, Kolasch & Birch, LLP

(57) ABSTRACT

A method for manufacturing a balloon catheter including preparing a tubular parison (20) made of a resin and a mold (30) that has an inner cavity into which the parison (20) is to be inserted and that has a first groove (41) formed on an inner wall surface forming the inner cavity; inserting the parison (20) into the inner cavity of the mold (30); allowing the resin to enter the first groove (41) by introducing a fluid into a lumen (23) of the parison (20) to expand the parison (20); and removing the parison (20) from the mold (30)

(Continued)

before the resin reaches a bottom (41a) of the first groove (41).

14 Claims, 9 Drawing Sheets

(56) References Cited

U.S. PATENT DOCUMENTS

| | | |
|---|---|---|
| 2003/0144683 A1 | 7/2003 | Sirhan et al. |
| 2005/0015107 A1* | 1/2005 | O'Brien ................ A61M 25/04 |
| | | 606/194 |
| 2006/0182873 A1* | 8/2006 | Klisch ................... A61M 25/10 |
| | | 427/2.1 |
| 2007/0191811 A1 | 8/2007 | Berglund |
| 2011/0288479 A1* | 11/2011 | Burton ........... A61B 17/320725 |
| | | 604/103.08 |
| 2012/0191111 A1 | 7/2012 | Aggepholm et al. |
| 2015/0150586 A1 | 6/2015 | Aggerholm et al. |
| 2015/0320985 A1 | 11/2015 | Nakagawa |
| 2016/0058982 A1* | 3/2016 | Aggerholm ....... A61M 25/1029 |
| | | 604/103.08 |
| 2017/0007805 A1 | 1/2017 | Tsubooka |
| 2020/0324094 A1* | 10/2020 | Ronan ................. B29C 49/4273 |

FOREIGN PATENT DOCUMENTS

| | | |
|---|---|---|
| JP | 2005-502428 A | 1/2005 |
| JP | 2005-511187 A | 4/2005 |
| JP | 2014-64612 A | 4/2014 |
| JP | 2017-12678 A | 1/2017 |
| WO | 2018/012399 A1 | 1/2018 |

OTHER PUBLICATIONS

International Search Report for PCT/JP2020/018980 (PCT/ISA/210) mailed on Jul. 28, 2020.
Written Opinion of the International Searching Authority for PCT/JP2020/018980 (PCT/ISA/237) mailed on Jul. 28, 2020.

* cited by examiner

[Fig. 1]
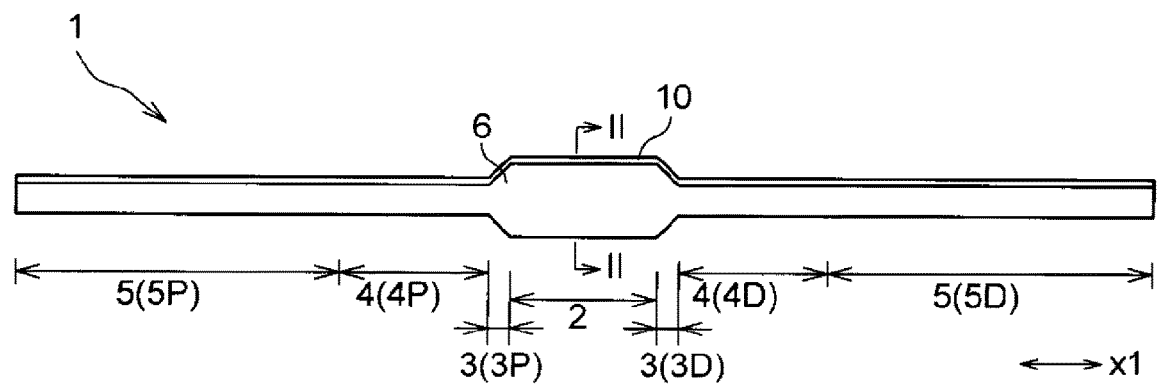
[Fig. 2]
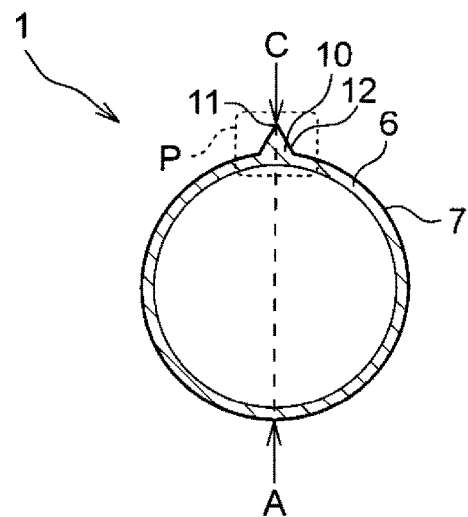

[Fig. 3]
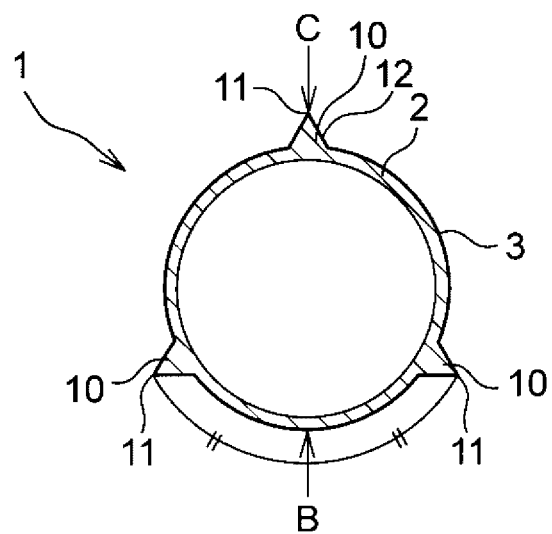
[Fig. 4]
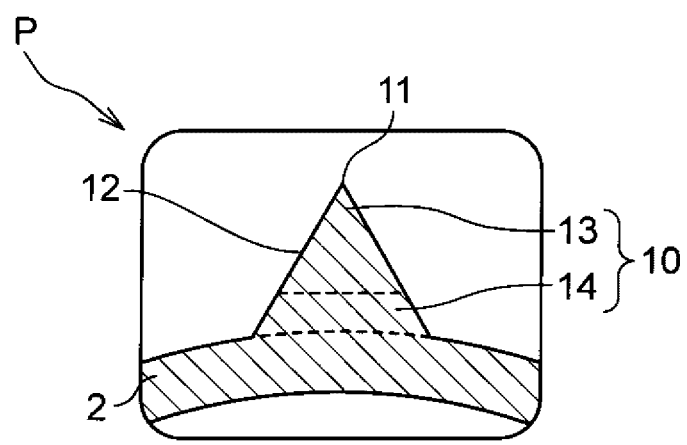

[Fig. 5]
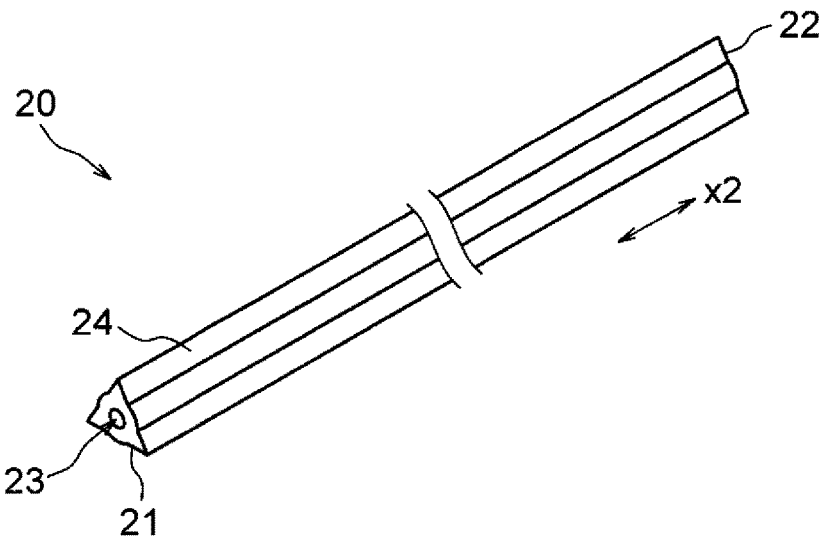
[Fig. 6]
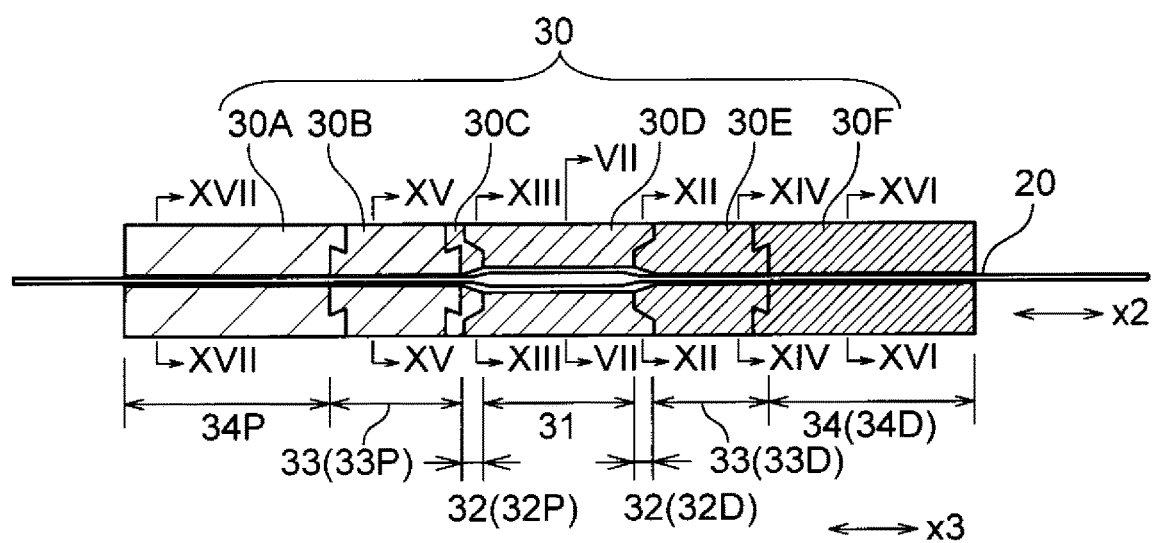

[Fig. 7]
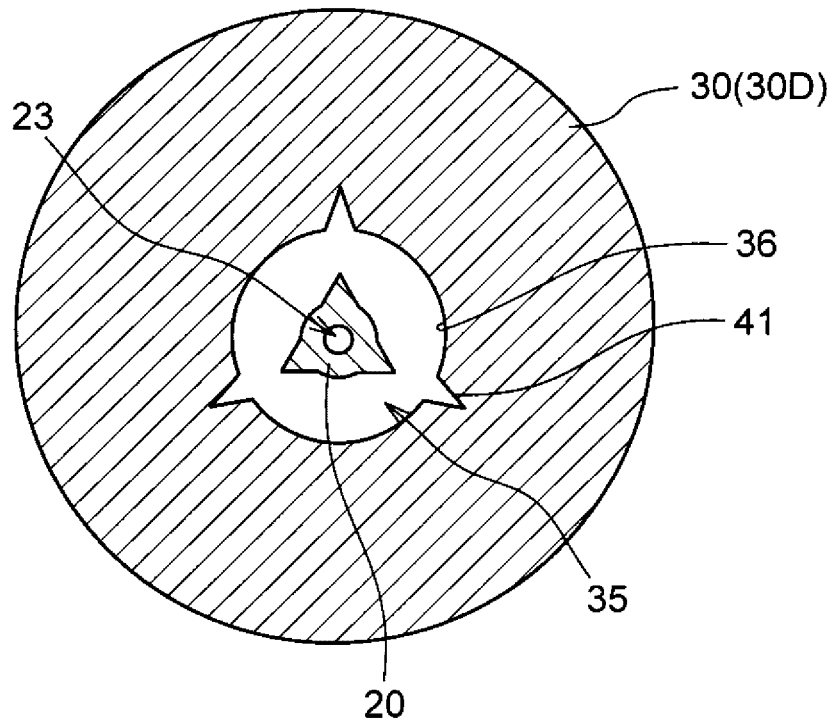
[Fig. 8]
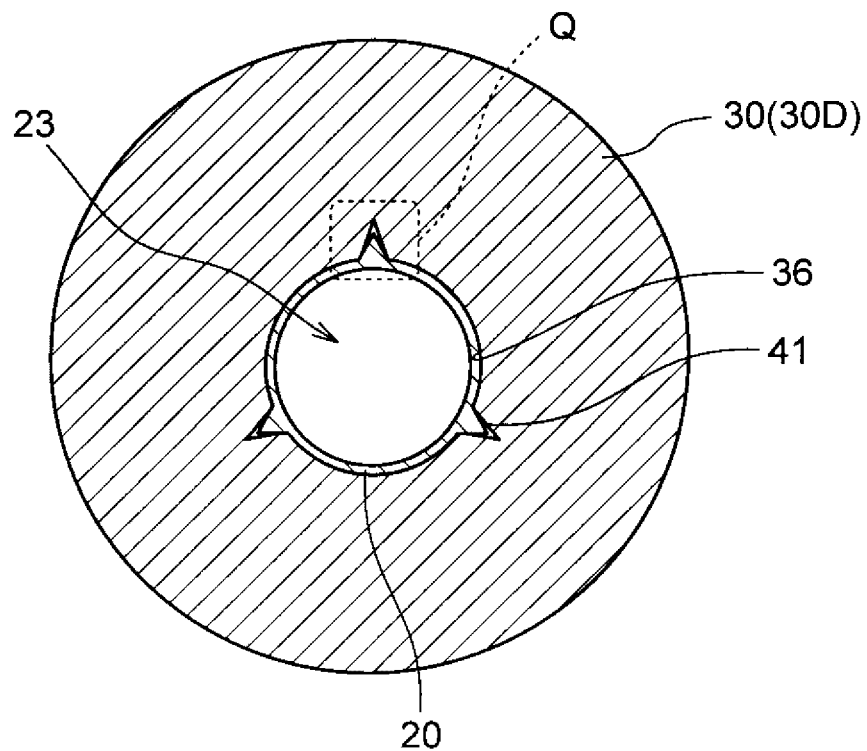

[Fig. 9]
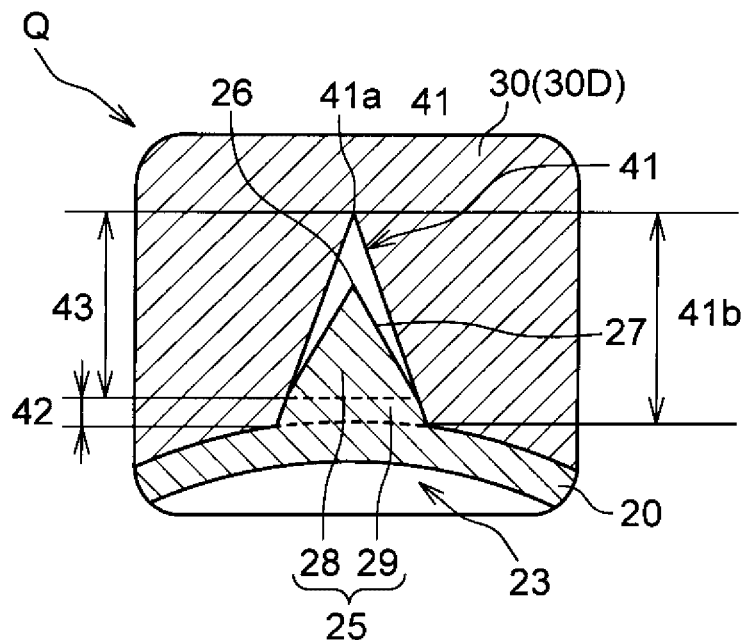
[Fig. 10]
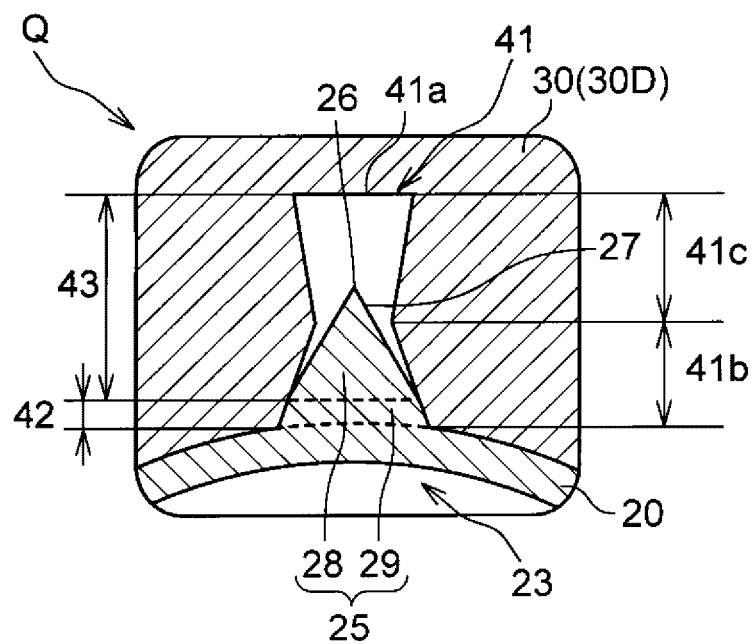

[Fig. 11]
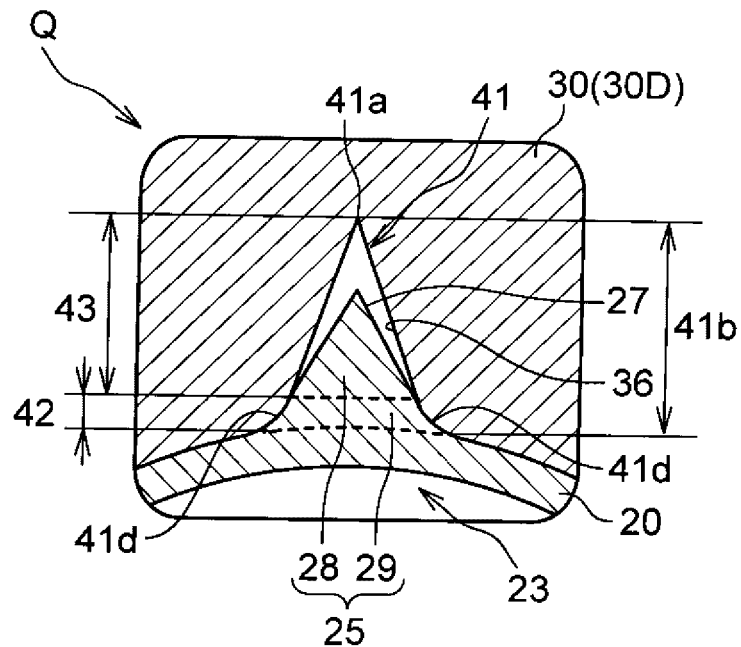
[Fig. 12]
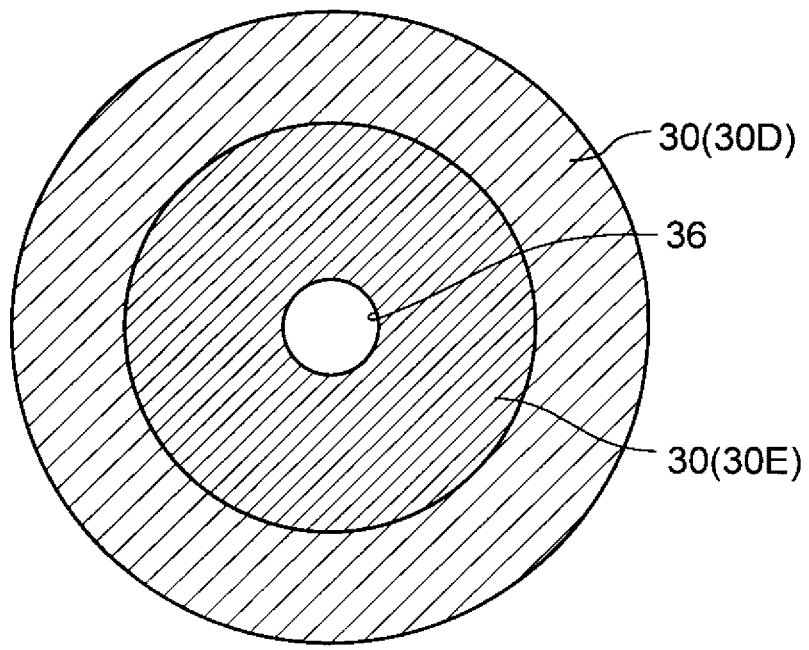

[Fig. 13]
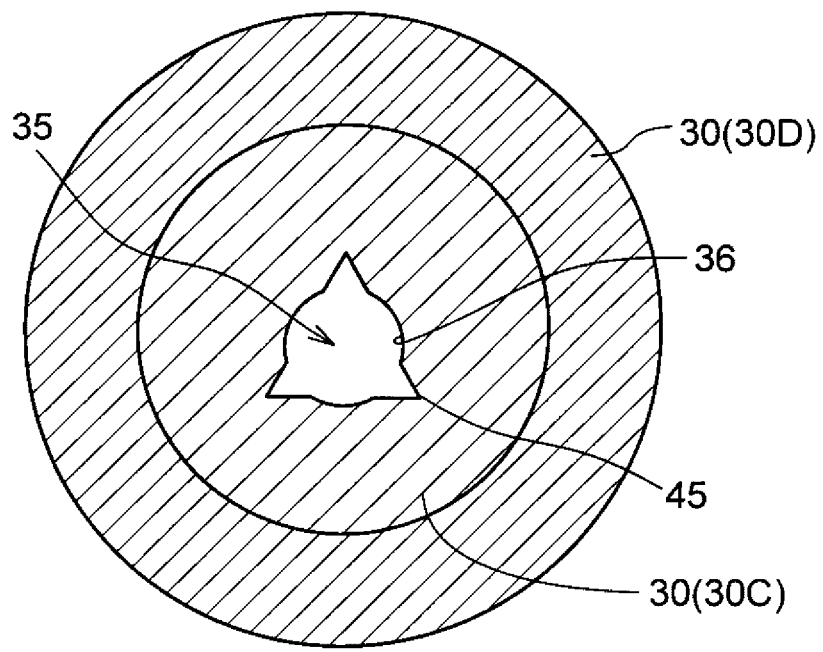
[Fig. 14]
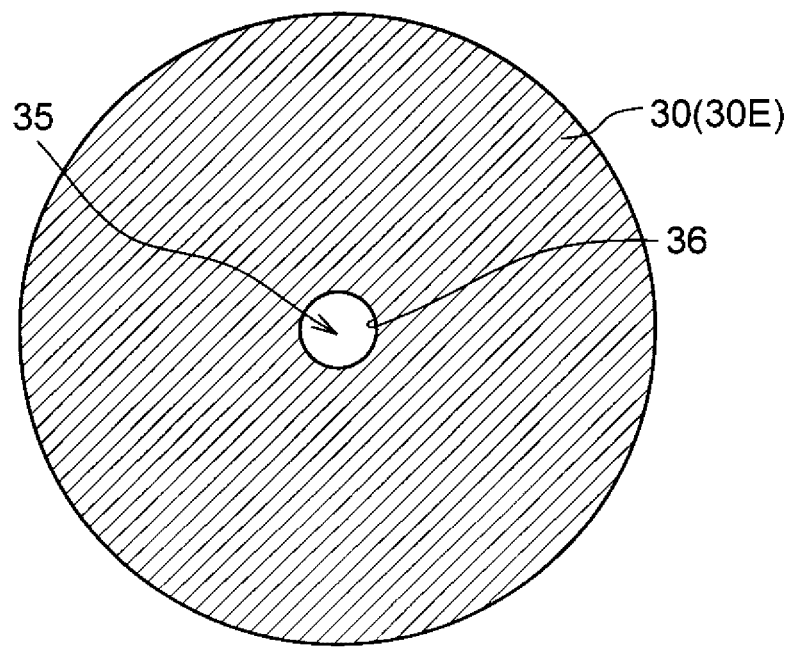

[Fig. 15]
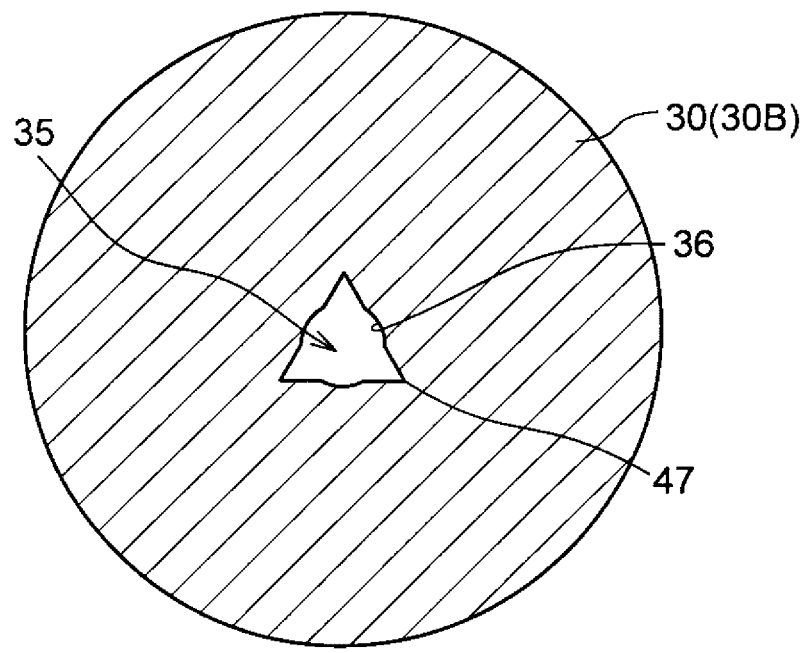
[Fig. 16]
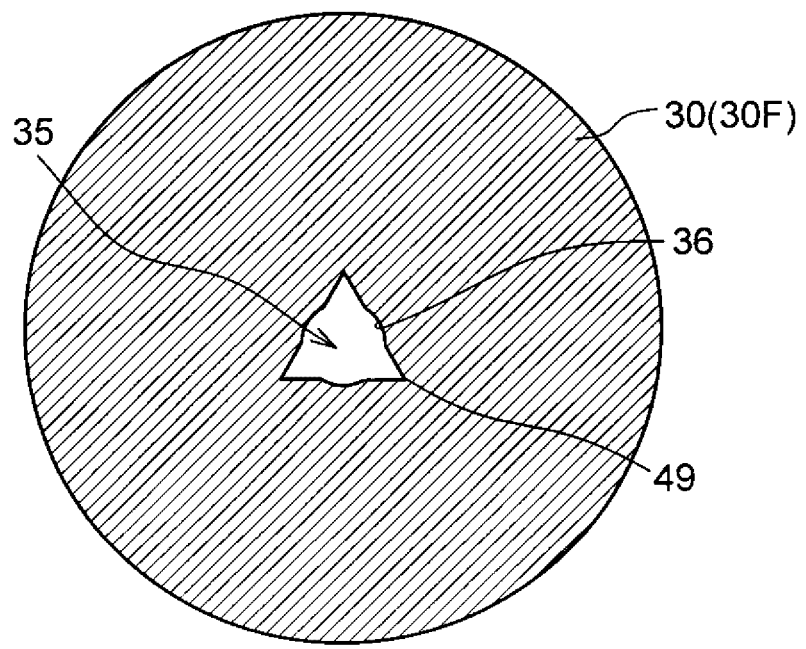

[Fig. 17]
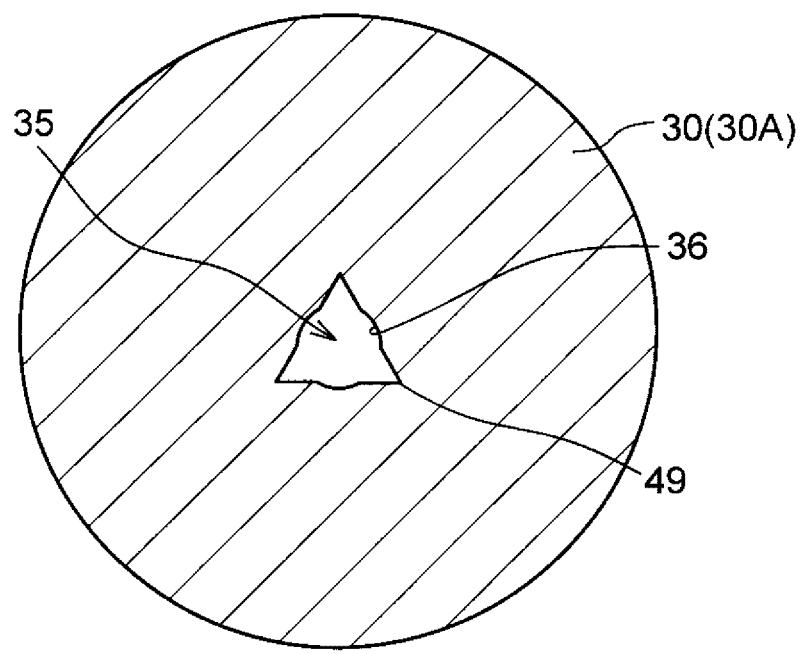

BALLOON FOR BALLOON CATHETER AND METHOD FOR MANUFACTURING BALLOON CATHETER

TECHNICAL FIELD

The present invention relates to a balloon for a balloon catheter and a method for manufacturing a balloon catheter using a tubular resin parison.

BACKGROUND ART

A balloon catheter is used to expand a stenosis site formed in a blood vessel, and a protruding part or a blade for biting into the stenosis site is preferably provided on the surface of a balloon. For example, Patent Document 1 discloses a balloon including a projection part, and a method for manufacturing a balloon including a step of forming a projection part by welding at least parts of adjacent inner surfaces at a part where inner surfaces of a balloon are placed so as to face each other. Patent Document 2 discloses a balloon having pleats formed as protruding parts, and the pleats are formed on a balloon by using a mold.

RELATED ART DOCUMENT

Patent Document

Patent Document 1: JP 2017-12678 A
Patent Document 2: JP 2005-511187 T

SUMMARY OF THE INVENTION

Problems to be Solved by the Invention

However, although the protruding part of the above balloon comes into contact with a stenosis site, there is room for improvement in that it is difficult to form a crack due to insufficient biting into a calcification lesion or a plaque. Therefore, an objective of the present invention is to provide a balloon for a balloon catheter and a method for manufacturing a balloon catheter that allow a crack to be easily formed in a calcification lesion or a plaque at a stenosis

Means for Solving the Problems

The gist of one embodiment of a balloon for a balloon catheter of the present invention that can solve the above problems is as follows. The balloon includes a balloon body; and a protruding part formed on an outer surface of the balloon body and made of the same material as the balloon body, wherein a surface roughness of an outer surface of the protruding part is lower than a surface roughness of the outer surface of the balloon body. By setting the surface roughness of the outer surfaces of the protruding part and the balloon body as described above, a resistance friction force generated when the protruding part bites into a calcification lesion or a plaque formed at a stenosis site can be kept low. Therefore, it is made easier to make a cut in the calcification lesion or the plaque at the stenosis site, which makes it easier to form a crack therein, so that it is possible to expand the stenosis site while preventing dissection of the vascular intima. In addition, a balloon catheter is usually delivered to a stenosis site in a state where a balloon folded so as to cover a protruding part with a balloon membrane is housed in a protective tube. However, when the protruding part of the balloon comes into contact with or rubs against the outer surface of a balloon body, a coating layer provided on the outer surface of the balloon body may be peeled off. On the other hand, with the balloon of the present invention, since the surface roughness of the protruding part is lower than that of the balloon body, it is possible to prevent the coating layer from being peeled off even when the protruding part comes into contact with the outer surface of the balloon body. This allows the balloon to remain highly passable in a body when the catheter is used while the balloon is outside the protective tube.

Preferably, in the balloon for a balloon catheter, the protruding part has a tip end region including an outer end point in a radial direction of the protruding part, and a base end region that is located inward of the tip end region in the radial direction and that has a surface roughness higher than a surface roughness of the tip end region.

The present invention also provides a method for manufacturing a balloon catheter. The gist of one embodiment of the method for manufacturing a balloon catheter of the present invention that can solve the above problems is as follows. The method includes a step of preparing a tubular parison made of a resin and a mold that has an inner cavity into which the parison is to be inserted and that has a first groove formed on an inner wall surface forming the inner cavity; a step of inserting the parison into the inner cavity of the mold; a step of allowing the resin to enter the first groove by introducing a fluid into a lumen of the parison to expand the parison; and a step of removing the parison from the mold before the resin reaches a bottom of the first groove. Since the above manufacturing method includes the step of removing the parison from the mold before the resin reaches the bottom of the first groove, the unevenness of the inner wall surface of the first groove is not transferred to the tip end side of the protruding part. Therefore, a resistance friction force generated when the protruding part bites into a calcification lesion or a plaque formed at a stenosis site can be kept low. As a result, it is made easier to make a cut in the calcification lesion or the plaque at the stenosis site, which makes it easier to form a crack therein. Therefore, it is possible to expand the stenosis site while preventing dissection of the vascular intima.

Preferably, in the above manufacturing method, a protruding part formed on an outer surface of the parison after the step of allowing the resin to enter the first groove has a base end region that blocks an entrance of the first groove by coming into contact with an inner wall surface of the first groove, and a tip end region that is located outward of the base end region in a radial direction and that is separated from the inner wall surface of the first groove.

Preferably, in the above manufacturing method, a surface roughness of the tip end region of the protruding part is lower than a surface roughness of the outer surface of the parison measured after the step of allowing the resin to enter the first groove.

Preferably, the above manufacturing method further includes a step of polishing an outer surface of the protruding part. The above manufacturing method preferably further includes a step of sharpening the protruding part. The above manufacturing method preferably further includes a step of roughening an outer surface of the protruding part.

Preferably, in the above manufacturing method, the protruding part extends along a longitudinal direction of the parison, and the method further includes a step of varying a height of the protruding part depending on a position in the longitudinal direction of the parison.

Preferably, in the above manufacturing method, the protruding part extends along a longitudinal direction of the parison, and the method further includes a step of making a cut in an outer surface of the protruding part.

Preferably, in the above manufacturing method, the first groove of the mold has a contact region being in contact with the base end region of the parison, and a non-contact region being separated from the tip end region of the parison; and the contact region has an arc-shaped part formed in an arc shape in a cross-section perpendicular to a longitudinal direction of the mold.

Preferably, in the above manufacturing method, the mold has a first section that extends in a longitudinal direction of the mold and that forms a straight tube part of a balloon; and the first groove is formed in the first section.

Preferably, in the above manufacturing method, in a longitudinal direction of the mold, the mold has a second section that is located on both sides of the first section and that forms a tapered part of the balloon, and a third section that is located on an end part side in the longitudinal direction of the mold than the second section and that forms a sleeve part of the balloon; the second section consists of a distal second section located at a position corresponding to a distal side of the balloon than the first section, and a proximal second section located at a position corresponding to a proximal side of the balloon than the first section; the third section consists of a distal third section that is located at a position corresponding to the distal side of the balloon than the distal second section and that forms a distal sleeve part, and a proximal third section that is located at a position corresponding to the proximal side of the balloon than the proximal second section and that forms a proximal sleeve part; a third groove shallower than the first groove is formed on an inner wall surface of at least either one of the distal third section and the proximal third section of the mold; and the resin reaches a bottom of the third groove in the step of allowing the resin to enter the first groove.

Preferably, in the above manufacturing method, a parison having a guide part protruding outwardly in a radial direction on an outer surface of the parison is prepared in the step of preparing the parison; and the guide part is placed in the third groove in the step of inserting the parison into the inner cavity of the mold.

Preferably, in the above manufacturing method, in a longitudinal direction of the mold, the mold has a second section that is located on both sides of the first section and that forms a tapered part of the balloon, the second section consists of a distal second section located at a position corresponding to a distal side of the balloon than the first section, and a proximal second section located at a position corresponding to a proximal side of the balloon than the first section; and no groove is formed on an inner wall surface of at least either one of the distal second section and the proximal second section of the mold.

Preferably, in the above manufacturing method, the first groove has a part that becomes wider toward an outer side in a radial direction.

Preferably, in the above manufacturing method, the first groove has a part that becomes narrower toward an outer side in a radial direction.

Effects of the Invention

According to the above balloon for a balloon catheter and the above method for manufacturing a balloon catheter, a resistance friction force generated when the protruding part of the balloon bites into a calcification lesion or a plaque formed at a stenosis site can be kept low. Therefore, it is made easier to make a cut in the calcification lesion or the plaque at the stenosis site, which makes it easier to form a crack therein, so that it is possible to expand the stenosis site while preventing dissection of the vascular intima.

BRIEF DESCRIPTION OF THE DRAWINGS

FIG. 1 is a side view of a balloon for a balloon catheter according to one embodiment of the present invention.

FIG. 2 is a cross-sectional view taken along line II-II in FIG. 1.

FIG. 3 is a cross-sectional view illustrating a modification of FIG. 2.

FIG. 4 is an enlarged cross-sectional view of a part P in FIG. 2.

FIG. 5 is a perspective view of a parison before being expanded according to one embodiment of the present invention.

FIG. 6 is a cross-sectional view (partially a side view) showing a state where the parison before being expanded is placed in a mold according to one embodiment of the present invention.

FIG. 7 is a cross-sectional view taken along line VII-VII in FIG. 6, illustrating a cross-section of a first section that forms a straight tube part of a balloon.

FIG. 8 is a cross-sectional view showing a state where the parison shown in FIG. 7 is expanded.

FIG. 9 is an enlarged cross-sectional view of a part Q in FIG. 8.

FIG. 10 is a cross-sectional view of a modification of FIG. 9.

FIG. 11 is a cross-sectional view of another modification of FIG. 9.

FIG. 12 is a cross sectional view taken along line XII-XII in FIG. 6, illustrating a cross-section of a distal second section that forms a distal tapered part of the balloon.

FIG. 13 is a cross-sectional view taken along line XIII-XIII in FIG. 6, illustrating a cross-section of a proximal second section that forms a proximal tapered part of the balloon.

FIG. 14 is a cross-sectional view taken along line XIV-XIV in FIG. 6, illustrating a cross-section of a distal third section that forms a distal sleeve part of the balloon.

FIG. 15 is a cross-sectional view taken along line XV-XV in FIG. 6, illustrating a cross-section of a proximal third section that forms a proximal sleeve part of the balloon.

FIG. 16 is a cross-sectional view taken along line XVI-XVI in FIG. 6, illustrating a cross-section of a distal fourth section that forms a distal sleeve outer part of the balloon.

FIG. 17 is a cross-sectional view taken along line XVII-XVII in FIG. 6, illustrating a cross-section of a proximal fourth section that forms a proximal sleeve outer part of the balloon.

DESCRIPTION OF EMBODIMENTS

Hereinafter, the present invention will be more specifically described based on the following embodiments. However, the present invention is not limited to the following embodiments and, as a matter of course, can also be carried out with appropriate modifications being made within the scope of the gist described above and below, and any of these modifications are included in the technical scope of the present invention. In any of the drawings, hatching, reference signs for members, or the like may be omitted for convenience. In this case, see the description and the other drawings. Since priority is given to facilitating the understanding of the characteristics of the present invention, the dimensions of various members in the drawings may be different from actual dimensions.

1. Balloon for Balloon Catheter

An embodiment of the balloon for a balloon catheter according to the present invention is characterized by including a balloon body and a protruding part formed on an outer surface of the balloon body and made of the same material as the balloon body, wherein a surface roughness of an outer surface of the protruding part is lower than a surface roughness of the outer surface of the balloon body. By setting the surface roughness of the outer surfaces of the protruding part and the balloon body as described above, a resistance friction force generated when the protruding part bites into a calcification lesion or a plaque formed at a stenosis site can be kept low. Therefore, it is made easier to make a cut in the calcification lesion or the plaque at the stenosis site, which makes it easier to form a crack therein, so that it is possible to expand the stenosis site while preventing dissection of the vascular intima. In addition, a balloon catheter is usually delivered to a stenosis site in a state where a balloon folded so as to cover a protruding part with a balloon membrane is housed in a protective tube. However, if the protruding part of the balloon comes into contact with or rubs against the outer surface of a balloon body, a coating layer provided on the outer surface of the balloon body may be peeled off. On the other hand, with the balloon of the present invention, since the surface roughness of the protruding part is lower than that of the balloon body, it is possible to prevent the coating layer from being peeled off even when the protruding part comes into contact with the outer surface of the balloon body. This allows the balloon to remain highly passable in a body when the catheter is used while the balloon is outside the protective tube. Hereinafter, a balloon for a balloon catheter is sometimes referred to simply as a "balloon".

A balloon for a balloon catheter will be described with reference to FIG. 1 and FIG. 2. FIG. 1 shows a side view of a balloon for a balloon catheter according to an embodiment of the present invention, and FIG. 2 shows a cross-sectional view taken along line II-II in FIG. 1.

A balloon catheter is a medical instrument mainly used in angioplasties (PTA, PTCA, etc.) that are conducted in treatment of a stenosis site in a blood vessel to expand the stenosis site. It has been known that various diseases develop because of stagnation in circulation of blood due to occurrence of a stenosis of a blood vessel, which is a flow path for circulating blood in the body. Especially, if a coronary artery for supplying blood to the heart suffers a stenosis, critical diseases such as angina pectoris and myocardial infarction may be caused. Angioplasties are minimally invasive therapies requiring no thoracotomies such as bypass surgery and are therefore widely conducted.

A balloon catheter includes a shaft and a balloon provided outside the shaft. The balloon catheter has a proximal side and a distal side, the balloon is provided on the distal side of the shaft, and a hub is provided on the proximal side of the shaft. The proximal side of the balloon refers to the hand side of a user or an operator in the longitudinal direction of the shaft or the direction in which the balloon catheter extends, and the distal side of the balloon refers to the side opposite to the proximal side, that is, the treatment target side. In addition, the direction from the proximal side to the distal side of the balloon is referred to as distal-proximal direction.

As shown in FIG. 1 and FIG. 2, a balloon 1 includes a balloon body 6 and a protruding part 10 formed on an outer surface 7 of the balloon body 6 and made of the same material as the balloon body 6. The balloon body 6 defines the basic shape of the balloon 1 and is preferably formed in a bag shape having openings on the proximal side and the distal side, respectively. The protruding part 10 is preferably provided on the outer surface 7 of the balloon body 6 in a dot-like, linear, or net-like pattern. By providing the protruding part 10 on the outer surface 7 of the balloon body 6, it is possible to crack and expand a calcified stenosis site in an angioplasty with the protruding part 10 given a scoring function. In addition, it is also possible to increase the strength of the balloon 1 and suppress excessive expansion of the balloon 1 during pressurization.

In the present invention, the protruding part 10 of the balloon 1 refers to a part formed higher in the radial direction than the film thickness at a predetermined position of the balloon body 6. In the case where one protruding part 10 is provided to the balloon body 6, the predetermined position is a position A facing an outer end 11 in the radial direction of the protruding part 10 in the circumferential direction of the balloon 1 as shown in FIG. 2. In the case where a plurality of protruding parts 10 are provided to the balloon body 6, the predetermined position is a position B corresponding to the midpoint in the circumferential direction of the balloon 1 between outer ends 11 of the protruding parts 10 adjacent to each other in the circumferential direction as shown in FIG. 3.

The maximum height in the radial direction of the protruding part 10 is preferably not less than 1.2 times, more preferably not less than 1.5 times, and further preferably not less than 2 times the film thickness at the predetermined position of the balloon body 6, and is also permitted to be not greater than 100 times, not greater than 50 times, not greater than 30 times, or not greater than 10 times the film thickness at the predetermined position of the balloon body 6. Accordingly, it is made easier to make a cut with an appropriate depth in a calcification lesion or a plaque at a stenosis site, which makes it easier to form a crack therein.

In the case where the protruding part 10 is formed in a dot-like or linear pattern, the protruding part 10 is preferably provided so as to extend along the distal-proximal direction of the balloon 1. In addition, the protruding part 10 may be provided so as to extend spirally around the long axis of the balloon 1. Furthermore, the protruding part 10 may be provided so as to extend along the circumferential direction of the balloon 1. Accordingly, the contact area between the protruding part 10 and a stenosis site can be adjusted, so that it is possible to achieve both desired passing performance of the catheter in a body cavity and desired non-slip performance of the balloon 1 against the stenosis site.

As shown in FIG. 1, the balloon 1 includes a straight tube part 2, a tapered part 3 that is located on both sides of the straight tube part 2 and that has an outer diameter decreasing toward the end part side in a distal-proximal direction x1, a sleeve part 4 that is located on the end part side in the distal-proximal direction x1 than the tapered part 3 and that is to be connected to the shaft of a balloon catheter, and a sleeve outer part 5 that is located on the end part side in the distal-proximal direction x1 than the sleeve part 4 and that is to be cut before the balloon 1 is attached to the shaft. A part of the tapered part 3 located on the distal side than the straight tube part 2 is referred to as a distal tapered part 3D, and a part of the tapered part 3 located on the proximal side than the straight tube part 2 is referred to as a proximal tapered part 3P. In addition, a part of the sleeve part 4 located on the distal side than the distal tapered part 3D is referred to as a distal sleeve part 4D, and a part of the sleeve part 4 located on the proximal side than the proximal tapered part 3P is referred to as a proximal sleeve part 4P. Furthermore, a part of the sleeve outer part 5 located on the distal side than the distal sleeve part 4D is referred to as a distal sleeve outer part 5D, and a part of the sleeve outer part 5 located on the proximal side than the proximal sleeve part 4P is referred to as a proximal sleeve outer part 5P.

The protruding part 10 is preferably provided to the straight tube part 2. Accordingly, during expansion of the balloon 1, the protruding part 10 easily bites into a stenosis site. The protruding part 10 may be provided to the straight tube part 2 and the tapered part 3 such that a stenosis site is easily cracked.

FIG. 3 shows a cross-sectional view illustrating a modification of FIG. 2. As shown in FIG. 2, only one protruding part 10 may be provided. In addition, as shown in FIG. 3, a plurality of protruding parts 10 may be provided. In this case, the plurality of protruding parts 10 are preferably provided so as to be aligned in the circumferential direction, and more preferably provided at equal intervals in the circumferential direction. By providing the plurality of protruding parts 10 as described above, it is made easier to crack a stenosis site at a plurality of positions. The plurality of protruding parts 10 are preferably provided so as to be separated from each other in the circumferential direction, and the separation distance between the protruding parts 10 adjacent to each other in the circumferential direction is more preferably longer than the maximum circumferential length of each protruding part 10.

Since the balloon body 6 and the protruding part 10 are made of the same material, the protruding part 10 can be prevented from damaging the outer surface 7 of the balloon body 6 while maintaining the flexibility of the balloon 1. The balloon body 6 and the protruding part 10 are preferably integrally molded. Accordingly, the protruding part 10 can be prevented from falling off from the balloon body 6. Such a balloon 1 can be manufactured, for example, by placing a parison obtained by extrusion, in a mold having a groove, and performing biaxial stretching blow molding. A preferable method for manufacturing the balloon will be described later in "2. Method for manufacturing balloon catheter".

Examples of a resin for forming the balloon body 6 and the protruding part 10 include: polyolefin-based resins such as polyethylene, polypropylene, and ethylene-propylene copolymer; polyester-based resins such as polyethylene terephthalate and polyester elastomer; polyurethane-based resins such as polyurethane and polyurethane elastomer; polyphenylene sulfide-based resins; polyamide-based resins such as polyamide and polyamide elastomer; fluorine-based resins; silicone-based resins; natural rubbers such as latex rubber; and the like. Only one of these resins may be used, or two or more of these resins may be used in combination. Among these resins, polyamide-based resins, polyester-based resins, and polyurethane-based resins are suitably used. Especially, an elastomer resin is preferably used in terms of thickness reduction and flexibility of the balloon 1. Examples of a material suitable for the balloon 1 among polyamide-based resins include nylon 12, nylon 11, and the like, and nylon 12 is suitably used since it can be relatively easy to blow mold. Moreover, polyamide elastomers such as polyether ester amide elastomer and polyamide ether elastomer are preferably used in terms of thickness reduction and flexibility of the balloon 1. Among these elastomers, polyether ester amide elastomer is preferably used since polyether ester amide elastomer has a high yield strength and allows the balloon 1 to have good dimensional stability.

A surface roughness of an outer surface 12 of the protruding part 10 is lower than a surface roughness of the outer surface 7 of the balloon body 6. By reducing the surface roughness of the protruding part 10 as described above, it is made easier to make a cut in a calcification lesion or a plaque at a stenosis site, which makes it easier to form a crack therein, so that it is possible to expand the stenosis site while preventing dissection of the vascular intima. The surface roughness of the outer surface 12 of the protruding part 10 is preferably not less than 0.01 times, more preferably not less than 0.05 times, and further preferably not less than 0.1 times the surface roughness of the outer surface 7 of the balloon body 6, and is also permitted to be not greater than 0.9 times, not greater than 0.8 times, or not greater than 0.7 times the surface roughness of the outer surface 7 of the balloon body 6. An example of the method for reducing the surface roughness of the outer surface 12 of the protruding part 10 is a method in which the protruding part 10 is polished by using a grinding machine or a file.

In the case where only one protruding part 10 is provided to the balloon body 6, the surface roughness of the outer surface 7 of the balloon body 6 is obtained by measuring a part including the position A of the outer surface 7 of the balloon body 6 as shown in FIG. 2. In the case where a plurality of protruding parts 10 are provided to the balloon body 6, the surface roughness of the outer surface 7 of the balloon body 6 is obtained by measuring a part including the position B of the outer surface 7 of the balloon body 6 as shown in FIG. 3. In addition, the surface roughness of the outer surface 12 of the protruding part 10 is obtained by measuring a part including the outer end 11 in the radial direction of the protruding part 10 (that is, the tip end of the protruding part 10) of the outer surface 12 of the protruding part 10. In the case where there are a plurality of protruding parts 10, it is sufficient that any one of the protruding parts 10 is measured.

The surface roughness is an arithmetic mean roughness Ra in a reference length of a roughness curve for the outer surface of the balloon body 6 or the protruding part 10, and the reference length is 0.1 mm. The arithmetic mean roughness Ra corresponds to an arithmetic mean roughness Ra specified in JIS B 0601 (2001), and is measured according to JIS B 0633 (2001). For the measurement, a measuring machine specified in JIS B 0651 (2001) (for example, a laser microscope VK-9510 manufactured by KEYENCE CORPORATION) is used.

The surface roughness of the entirety of the outer surface 12 of the protruding part 10 (that is, the entire outer peripheral surface of the protruding part 10) is preferably lower than the surface roughness of the outer surface 7 of the balloon body 6. Accordingly, it is made easier to make a cut in a calcification lesion or a plaque at a stenosis site, so that the formation of a crack is further promoted.

In the case where a plurality of protruding parts 10 are provided to the balloon body 6 as shown in FIG. 3, the surface roughnesses of the outer surfaces 12 of all of the protruding parts 10 are preferably lower than the surface roughness of the outer surface 7 of the balloon body 6. Accordingly, it is made easier to make a cut in a calcification lesion or a plaque at a stenosis site, so that the formation of a crack is further promoted.

FIG. 4 shows an enlarged cross-sectional view of a part P, of the balloon 1 in FIG. 2, where the protruding part 10 is provided. As shown in FIG. 4, the protruding part 10 preferably includes a tip end region 13 that includes the outer end 11 in the radial direction of the protruding part 10, and a base end region 14 that is located inward of the tip end region 13 in the radial direction and that has a surface roughness higher than a surface roughness of the tip end region 13. Accordingly, it is made easier to make a cut in a calcification lesion or a plaque at a stenosis site by the tip end region 13, which makes it easier to form a crack therein, so that it is possible to expand the stenosis site while preventing dissection of the vascular intima. In addition, the resistance friction force between the base end region 14 and the stenosis site can be increased, so that the non-slip performance of the balloon 1 against the stenosis site can be improved.

The surface roughness of the base end region 14 is preferably not less than 2 times, more preferably not less than 3 times, and further preferably not less than 5 times the surface roughness of the tip end region 13, and is also permitted to be not greater than 20 times, not greater than 18 times, or not greater than 15 times the surface roughness of the tip end region 13.

The surface roughness of the base end region 14 may be equal to the surface roughness of the outer surface 7 of the balloon body 6, or is preferably not less than 0.1 times, more preferably not less than 0.2 times, and further preferably not less than 0.3 times the surface roughness of the outer surface 7 of the balloon body 6 and is also permitted to be not greater than 0.9 times, not greater than 0.8 times, or not greater than 0.7 times the surface roughness of the outer surface 7 of the balloon body 6.

The orientation of molecules in the tip end region 13 may be different from the orientation of molecules in the base end region 14. For example, in the tip end region 13, the molecules may be oriented outward in the radial direction or parallel to the movement direction of the resin during blow molding, and, in the base end region 14, the molecules may be oriented outward in the radial direction or in a direction perpendicular to the movement direction of the resin during blow molding. For measuring the orientation of the molecules, for example, an X-ray diffraction method or Raman spectroscopy can be used.

The degree of crystallinity in the tip end region 13 may be different from the degree of crystallinity in the base end region 14. The degree of crystallinity of the tip end region 13 is preferably higher than the degree of crystallinity in the base end region 14. Accordingly, cooling strain is less likely to occur in the tip end region 13 during the production of the protruding part 10, so that excessive deformation of the tip end region 13 can be prevented. The degree of crystallinity can be calculated from, for example, a calorific value obtained from a DSC curve obtained by differential scanning calorimetry.

2. Method for Manufacturing Balloon Catheter

An embodiment of the method for manufacturing a balloon catheter according to the present invention is characterized by including: a step of preparing a tubular parison made of a resin and a mold that has an inner cavity into which the parison is to be inserted and that has a first groove formed on an inner wall surface forming the inner cavity; a step of inserting the parison into the inner cavity of the mold; a step of allowing the resin to enter the first groove by introducing a fluid into a lumen of the parison to expand the parison; and a step of removing the parison from the mold before the resin reaches the bottom of the first groove. Since the manufacturing method includes the step of removing the parison from the mold before the resin reaches the bottom of the first groove, the unevenness of the inner wall surface of the first groove is not transferred to the tip end side of the protruding part. Therefore, a resistance friction force generated when the protruding part bites into a calcification lesion or a plaque formed at a stenosis site can be kept low. As a result, it is made easier to make a cut in the calcification lesion or the plaque at the stenosis site, which makes it easier to form a crack therein. Therefore, it is possible to expand the stenosis site while preventing dissection of the vascular intima. Furthermore, the balloon described in "1. Balloon for balloon catheter" can be manufactured by the above manufacturing method.

The above manufacturing method will be described with reference to FIG. 5 to FIG. 9. FIG. 5 shows a perspective view of a parison before expansion according to an embodiment of the present invention, and FIG. 6 shows a cross-sectional view (partial side view) showing a state where the parison before expansion is placed in a mold according to an embodiment of the present invention. In addition, FIG. 7 shows a cross-sectional view taken along a line VII-VII in FIG. 6 and illustrates a cross-section of a first section that forms a straight tube part of a balloon. FIG. 8 shows a cross-sectional view of a state where the parison shown in FIG. 7 is expanded, and FIG. 9 shows an enlarged cross-sectional view of a part Q in FIG. 8.

First, a parison 20 and a mold 30 are prepared. The parison 20 is a tubular member made of a resin. The parison 20 is produced, for example, by extrusion. The parison 20 has a first end 21 and a second end 22, and extends in a longitudinal direction x2 from the first end 21 toward the second end 22.

As shown in FIG. 5, a cross-sectional shape of the parison 20 in a direction perpendicular to the longitudinal direction x2 may be substantially uniform in the longitudinal direction x2. Accordingly, the productivity of the parison 20 can be increased. Alternatively, the cross-sectional shape of the parison 20 in the direction perpendicular to the longitudinal direction x2 may be different depending on the position in the longitudinal direction x2. The outer diameter of a part in the longitudinal direction x2 (for example, a part corresponding to the straight tube part and a tapered part of the balloon) of the parison 20 may be larger than that of other parts. In order to make the cross-sectional shape of the parison 20 different in the longitudinal direction x2, blow molding may be performed in advance by using another mold.

For the material for forming the parison 20, the description of the resin for forming the balloon body 6 and the protruding part 10 described in "1. Balloon for balloon catheter" can be referred to.

The mold 30 has an inner cavity 35 into which the parison 20 is to be inserted. Specifically, a part in the longitudinal direction x2 of the parison 20 is preferably placed in the mold 30. As shown in FIG. 6, the mold 30 has a longitudinal direction x3 corresponding to the longitudinal direction x2 of the parison 20. In order to make it easier to place the parison 20 in the mold 30, the longitudinal direction x3 of the mold 30 preferably coincides with the longitudinal direction x2 of the parison 20.

As shown in FIG. 6, the mold 30 preferably has, in the longitudinal direction x3 thereof, a first section 31 that forms the straight tube part of the balloon, and a second section 32 on both sides of the first section 31 and that forms the tapered part of the balloon. In addition, the mold 30 may have a third section 33 that is located on the end part side in the longitudinal direction x3 than the second section 32 and that forms a sleeve part of the balloon, and a fourth section 34 that is located on the end part side in the longitudinal direction x3 than the third section 33 and that forms a sleeve outer part of the balloon. The second section 32 preferably includes a distal second section 32D located at a position corresponding to the distal side of the balloon than the first section 31, and a proximal second section 32P located at a position corresponding to the proximal side of the balloon than the first section 31. The third section 33 preferably includes a distal third section 33D that is located at a position corresponding to the distal side of the balloon than the distal second section 32D and that forms a distal sleeve part of the balloon, and a proximal third section 33P that is located at a position corresponding to the proximal side of the balloon than the proximal second section 32P and that forms a proximal sleeve part of the balloon. The fourth section 34 preferably includes a distal fourth section 34D that is located at a position corresponding to the distal side of the balloon than the distal third section 33D and that forms a distal sleeve outer part of the balloon, and a proximal fourth section 34P that is located at a position corresponding to the proximal side of the balloon than the proximal third section 33P and that forms a proximal sleeve outer part of the balloon.

The mold 30 may be formed of one member, or may be formed of a plurality of members. For example, the mold 30 may be formed of a plurality of half-split bodies, or may be formed by a plurality of mold members being connected to each other in the distal-proximal direction. Above all, the mold 30 is preferably formed of a plurality of mold members having inner cavity cross-sectional shapes varied stepwise. In FIG. 6, the mold 30 includes a first mold 30A, a second mold 30B, a third mold 30C, a fourth mold 30D, a fifth mold 30E, and a sixth mold 30F in order from the proximal side. As shown in FIG. 6, the adjacent mold members may be connected by engaging the mold members with each other. Although not shown, the adjacent mold members may be connected by allowing magnets, which are attached to the mold members, to attract each other.

The inner cavity cross-sectional shape of the mold 30 can be a circular shape, an oblong shape, a polygonal shape, or a combination thereof. The oblong shape includes an elliptical shape, an egg shape, and a rectangular shape with rounded corners.

As shown in FIG. 7, a first groove 41 is formed on an inner wall surface 36 forming the inner cavity 35 of the mold 30. As shown in FIG. 6 and FIG. 7, the parison 20 is inserted into the inner cavity 35 of the mold 30. A fluid is introduced into a lumen 23 of the parison 20 to expand the parison 20 to allow the resin to enter the first groove 41 as shown in FIG. 8. As described above, by expanding the parison 20, the resin forming the parison 20 can be allowed to enter the first groove 41, thereby forming a protruding part 25 on the outer surface of the parison 20.

In the present invention, the protruding part 25 of the parison 20 refers to a part formed higher in the radial direction than the film thickness at a predetermined position of the expanded parison 20. For the predetermined position, the description of the predetermined position of the balloon body 6 described in "1. Balloon for balloon catheter" can be referred to by replacing the "balloon body" therein with "parison".

The parison 20 is removed from the mold 30 before the resin reaches a bottom 41a of the first groove 41. Accordingly, the unevenness of the inner wall surface of the first groove 41 is not transferred to the tip end side of the protruding part 25, so that a resistance friction force generated when the protruding part 25 bites into calcification lesion or a plaque formed at a stenosis site can be kept low. Therefore, it is made easier to make a cut in the calcification lesion or the plaque at the stenosis site, which makes it easier to form a crack therein. As a result, it is possible to expand the stenosis site while preventing dissection of the vascular intima. The expanded parison 20 can be used as a balloon for a balloon catheter. A balloon catheter can be manufactured by attaching the expanded parison 20 to the distal side of a shaft.

As shown in FIG. 7, one or more first grooves 41 can be provided. A plurality of first grooves 41 may be provided so as to be aligned in the circumferential direction. In this case, the first grooves 41 are preferably provided at equal intervals in the circumferential direction. By providing the first grooves 41 as described above, a plurality of protruding parts, which are produced by entering the first grooves 41, can be also provided, so that it is made easier to crack a stenosis site at a plurality of positions. The first grooves 41 are preferably provided so as to be separated from each other in the circumferential direction, and the separation distance between the first grooves 41 adjacent to each other in the circumferential direction is more preferably longer than the maximum circumferential length of each first groove 41.

The first groove 41 preferably extends in the longitudinal direction x3 of the mold 30. Accordingly, the protruding part 25 can be allowed to extend in the longitudinal direction x3 of the mold 30.

The depth of the first groove 41 may be uniform in the longitudinal direction x3 of the mold 30, or may be different depending on the position in the longitudinal direction x3.

As shown in FIG. 9, the protruding part 25 formed on the outer surface of the parison 20 after the step of allowing the resin to enter the first groove 41 preferably has a base end region 29 that blocks an entrance of the first groove 41 by coming into contact with the inner wall surface of the first groove 41, and a tip end region 28 that is located outward of the base end region 29 in the radial direction and that is separated from the inner wall surface of the first groove 41. The tip end region 28 preferably includes an outer end 26 in the radial direction of the protruding part 25. The base end region 29 is a part that has been in contact with the inner wall surface of the first groove 41, so that the unevenness of the inner wall surface of the first groove 41 is transferred thereto. On the other hand, the tip end region 28 is a part that has been separated from the inner wall surface of the first groove 41 of the mold 30, so that the unevenness of the inner wall surface of the first groove 41 is not transferred thereto. By adjusting the amount of the resin entering the first groove 41 as described above, the unevenness of the outer surfaces of the tip end region 28 and the base end region 29 of the protruding part 25 can be made different from each other. After the parison 20 is removed from the mold 30, the boundary between the tip end region 28 and the base end region 29 of the protruding part 25 can be confirmed by observing a cross-section, perpendicular to the distal-proximal direction, of the parison 20 using a microscope.

As shown in FIG. 9, the first groove 41 preferably has a part 41b that becomes narrower toward the outer side in the radial direction. Accordingly, it is made easier to sharpen the protruding part 25, and it is made easier to make a cut in a calcification lesion or a plaque at a stenosis site by the protruding part 25, so that it is made easier to form a crack therein. The width may decrease toward the outer side in the radial direction over the entire depth of the first groove 41 as shown in FIG. 9. Alternatively, the part 41b that becomes narrower toward the outer side in the radial direction may be provided on the entrance side of the first groove 41 as shown in FIG. 10 described later.

FIG. 10 shows a cross-sectional view of a modification of FIG. 9. As shown in FIG. 10, the first groove 41 preferably has a part 41c that becomes wider toward the outer side in the radial direction. In this case, the part 41c that becomes wider toward the outer side in the radial direction is preferably disposed on the bottom 41a side of the first groove 41. Accordingly, the resin is less likely to reach the bottom 41a of the first groove 41, and deformation of the protruding part 25 can also be prevented.

As shown in FIG. 10, the first groove 41 may have both the part 41b that becomes narrower toward the outer side in the radial direction and the part 41c that becomes wider toward the outer side in the radial direction. In this case, the part 41c that becomes wider toward the outer side in the radial direction is preferably located on the outer side in the radial direction (that is, on the bottom 41a side of the first groove 41) than the part 41b that becomes narrower toward the outer side in the radial direction. Accordingly, it is possible to transfer the unevenness of the inner wall surface of the first groove 41 to the parison 20 on the entrance side of the first groove 41 while making the resin less likely to reach the bottom 41a of the first groove 41. Therefore, it is made easier to form the parison 20 having the tip end region 28 and the base end region 29.

A surface roughness of the tip end region 28 of the protruding part 25 is preferably lower than a surface roughness of the outer surface of the parison 20 measured after the step of allowing the resin to enter the first groove 41. By reducing the surface roughness of the tip end region 28 of the protruding part 25 as described above, it is made easier to make a cut in a calcification lesion or a plaque at a stenosis site, which makes it easier to form a crack therein. Therefore, it is possible to expand the stenosis site while preventing dissection of the vascular intima.

For the measurement location of the surface roughness of the outer surface of the parison 20, the description of the measurement location of the surface roughness of the outer surface 7 of the balloon body 6 described in "1. Balloon for balloon catheter" can be referred to by replacing the "balloon body" therein with "parison".

The surface roughness is an arithmetic mean roughness Ra in a reference length of a roughness curve for the inner wall surface of the mold 30 or the outer surface of the parison 20, and the reference length is 0.1 mm. The arithmetic mean roughness Ra corresponds to an arithmetic mean roughness Ra specified in JIS B 0601 (2001), and is measured according to JIS B 0633 (2001). For the measurement, a measuring machine specified in JIS B 0651 (2001) (for example, a laser microscope VK-9510 manufactured by KEYENCE CORPORATION) is used.

An example of the method for increasing the surface roughnesses of the inner wall surface of the mold 30 and the outer surface of the parison 20 is a method in which these surfaces are mechanically or chemically roughened, and examples thereof include methods using etching, blasting, a wire brush, and sandpaper.

A surface roughness of the base end region 29 is preferably not less than 2 times, more preferably not less than 3 times, and further preferably not less than 5 times the surface roughness of the tip end region 28, and is also permitted to be not greater than 20 times, not greater than 18 times, or not greater than 15 times the surface roughness of the tip end region 28.

The surface roughness of the base end region 29 may be equal to the surface roughness of the outer surface of the parison 20 measured after the step of allowing the resin to enter the first groove 41, or is preferably not less than 0.1 times, more preferably not less than 0.2 times, and further preferably not less than 0.3 times the surface roughness of the outer surface of the parison 20 and is also permitted to be not greater than 0.9 times, not greater than 0.8 times, or not greater than 0.7 times the surface roughness of the outer surface of the parison 20.

The above manufacturing method preferably further includes a step of polishing an outer surface 27 of the protruding part 25. This allows the unevenness of the outer surface 27 of the protruding part 25 to be varied. By polishing the outer surface 27 of the protruding part 25, the tip end of the protruding part 25 may be formed sharply, or the surface roughness of the tip end region 28 of the protruding part 25 may be made lower than the surface roughness of the outer surface of the parison 20 measured after the step of allowing the resin to enter the first groove 41. A grinding machine or a file can be used for polishing.

The above manufacturing method may further include a step of sharpening the protruding part 25. In this case, the tip end region 28 of the protruding part 25 is preferably sharpened. Accordingly, it is made easier to make a cut in a calcification lesion or a plaque at a stenosis site by the protruding part 25, which makes it easier to form a crack therein. Therefore, it is possible to expand the stenosis site while preventing dissection of the vascular intima. Examples of the method for sharpening the protruding part 25 include a method in which the outer surface 27 of the protruding part 25 is polished, and a method in which the outer surface 27 of the protruding part 25 is shaved with a laser processing device or a cutting tool.

The above manufacturing method may further include a step of roughening the outer surface 27 of the protruding part 25. Accordingly, a resistance friction force generated when a stenosis site and the protruding part 25 come into contact with each other can be increased, so that the non-slip performance of the balloon can be improved. In order to achieve both improvement of non-slip performance and prevention of peeling of a coating layer provided on the outer surface of the balloon, only a part in the circumferential direction of the protruding part 25 of the parison 20 may be roughened.

Preferably, in the above manufacturing method, the protruding part 25 extends along the longitudinal direction x2 of the parison 20, and the above manufacturing method further includes a step of varying the height of the protruding part 25 depending on the position in the longitudinal direction x2 of the parison 20. Here, the height of the protruding part 25 means the height in the radial direction from the inner surface of the balloon body. By varying the height of the protruding part 25, the protruding part 25 can easily bite into a stenosis site, so that the non-slip performance of the balloon can be improved.

Preferably, the protruding part 25 extends along the longitudinal direction x2 of the parison 20, and the above manufacturing method further includes a step of making a cut in the outer surface 27 of the protruding part 25. By making a cut in the protruding part 25 as described above, the passing performance of the catheter in a body cavity can be improved. A cutting tool such as a cutter or a knife can be used for forming a cut.

The protruding part 25 may be divided into a plurality of parts by making a cut. One or more cuts can be provided in one protruding part 25. It is sufficient that the depth of the cut is smaller than the height of the protruding part 25. Accordingly, when the balloon formed from the expanded parison 20 is inserted into a body, it is possible to prevent body fluids and the like from entering the inside of the balloon through the part in which the cut is made. The width of the cut is not particularly limited, but is preferably smaller than the width of the protruding part 25.

The cut may be formed along the direction in which the protruding part 25 extends. Above all, the cut preferably extends along the longitudinal direction x2 of the parison 20. Alternatively, the cut may extend spirally around the long axis of the parison 20. The cut extending as described above can improve the passing performance of the catheter in a body cavity.

The cut may extend along the circumferential direction of the parison 20. The cut extending as described above can improve the non-slip performance of the balloon against a stenosis site.

FIG. 11 shows a cross-sectional view illustrating another modification of FIG. 9. Preferably, as shown in FIG. 11, the first groove 41 of the mold 30 has a contact region 42 being in contact with the base end region 29 of the parison 20, and a non-contact region 43 being separated from the tip end region 28 of the parison 20, and the contact region 42 includes an arc-shaped part 41d formed in an arc shape in a cross section perpendicular to the longitudinal direction x3 of the mold 30. Accordingly, a sudden change in outer shape from the outer surface of the parison 20 to the base end region 29 of the protruding part 25 can be reduced, so that the protruding part 25 can be prevented from breaking due to an external force.

The arc-shaped part 41d is preferably formed in a part including an inner end in the radial direction of the contact region 42. Accordingly, the effect of reducing the change in outer shape from the outer surface of the parison 20 to the protruding part 25 can be enhanced. In the first groove 41 of the mold 30, a linear part may be formed on the outer side in the radial direction than the arc-shaped part 41d.

Preferably, as shown in FIG. 6 to FIG. 8, the mold 30 has the first section 31 that extends in the longitudinal direction x3 and that forms the straight tube part of the balloon, and the first groove 41 is formed in the first section 31. Accordingly, the protruding part 25 can be formed in the parison 20 at the position corresponding to the straight tube part of the balloon.

Preferably, the mold 30 has, in the longitudinal direction x3, the second section 32 that is located on both sides of the first section 31 and that forms the tapered part of the balloon, the second section 32 includes the distal second section 32D located at the position corresponding to the distal side of the balloon than the first section 31, and the proximal second section 32P located at the position corresponding to the proximal side of the balloon than the first section 31, and a second groove 45 is formed in at least either one of the distal second section 32D and the proximal second section 32P of the mold 30. Accordingly, a second protruding part is formed at the position corresponding to the tapered part of the balloon, so that the non-slip performance of the balloon against a stenosis site can be improved.

Preferably, the mold 30 has, in the longitudinal direction x3, the second section 32 that is located on both sides of the first section 31 and that forms the tapered part of the balloon, the second section 32 includes the distal second section 32D located at the position corresponding to the distal side of the balloon than the first section 31, and the proximal second section 32P located at the position corresponding to the proximal side of the balloon than the first section 31, and no groove is formed on the inner wall surface of at least either one of the distal second section 32D and the proximal second section 32P of the mold 30. Accordingly, no protruding part is formed at the position, corresponding to the tapered part of the balloon, in the parison 20, so that the slipperiness of the tapered part of the balloon is appropriately ensured, and the passing performance of the balloon can be further enhanced.

Preferably, the mold 30 has, in the longitudinal direction x3, the second section 32 that is located on both sides of the first section 31 and that forms the tapered part of the balloon, and the third section 33 that is located on the end part side in the longitudinal direction x3 than the second section 32 and that forms the sleeve part of the balloon, the second section 32 includes the distal second section 32D located at the position corresponding to the distal side of the balloon than the first section 31, and the proximal second section 32P located at the position corresponding to the proximal side of the balloon than the first section 31, the third section 33 includes the distal third section 33D that is located at the position corresponding to the distal side of the balloon than the distal second section 32D and that forms the distal sleeve part of the balloon, and the proximal third section 33P that is located at the position corresponding to the proximal side of the balloon than the proximal second section 32P and that forms the proximal sleeve part of the balloon, a third groove 47 shallower than the first groove 41 is formed on the inner wall surface of at least either one of the distal third section 33D and the proximal third section 33P of the mold 30, and the resin reaches the bottom of the third groove 47 in the step of allowing the resin to enter the first groove 41. Accordingly, a third protruding part lower than the protruding part 25 (first protruding part) can be formed at the position, corresponding to the sleeve part of the balloon, in the parison 20, so that the passing performance of the sleeve part of the balloon in a body can be enhanced.

Preferably, in the step of preparing the parison 20, a parison 20 having a guide part protruding outwardly in the radial direction on its outer surface is prepared, and, in the step of inserting the parison 20 into the inner cavity 35 of the mold 30, the guide part is placed in the third groove 47. Accordingly, when the parison 20 is expanded by introducing a fluid into the lumen 35 of the parison 20, the guide part comes into contact with the third groove 47, which prevent the parison from rotating. Therefore, a protruding part formed on the outer surface of the balloon or the balloon body can be produced in a desired shape.

FIG. 12 shows a cross-sectional view taken along a line XII-XII in FIG. 6 and illustrates a cross-section of the distal second section 32D that forms the distal tapered part of the balloon. FIG. 13 shows a cross-sectional view taken along a line XIII-XIII in FIG. 6 and illustrates a cross-section of the proximal second section 32P that forms the proximal tapered part of the balloon. In FIG. 12 and the drawings subsequent thereto, the parison 20 in the mold 30 is not shown. Preferably, as shown in FIG. 6, FIG. 12, and FIG. 13, the second section 32 includes the distal second section 32D and the proximal second section 32P, the second groove 45 is formed on the inner wall surface 36 of the proximal second section 32P, and no groove is formed on the inner wall surface 36 of the distal second section 32D. Accordingly, the slipperiness of the distal tapered part of the balloon is appropriately ensured, so that the passing performance of the balloon can be enhanced. In addition, a second protruding part is formed on the proximal tapered part, so that the non-slip performance of the balloon against a stenosis site can be improved.

FIG. 14 shows a cross-sectional view taken along a line XIV-XIV in FIG. 6 and illustrates a cross-section of the distal third section 33D that forms the distal sleeve part of the balloon. In addition, FIG. 15 shows a cross-sectional view taken along a line XV-XV in FIG. 6 and illustrates a cross-section of the proximal third section 33P that forms the proximal sleeve part of the balloon. Preferably, as shown in FIG. 6, FIG. 14, and FIG. 15, the third section 33 of the mold 30 includes the distal third section 33D and the proximal third section 33P, and the third groove 47 is formed on the inner wall surface 36 of at least either one of the distal third section 33D and the proximal third section 33P. In this case, in the step of allowing the resin to enter the first groove 41, the resin preferably reaches the bottom of the third groove 47. Accordingly, a protruding part can also be provided at the position, corresponding to the sleeve part of the balloon, in the parison 20.

FIG. 16 shows a cross-sectional view taken along a line XVI-XVI in FIG. 6 and illustrates a cross-section of the distal fourth section 34D that forms the distal sleeve outer part of the balloon. FIG. 17 shows a cross-sectional view taken along a line XVII-XVII in FIG. 6 and illustrates a cross-section of the proximal fourth section 34P that forms the proximal sleeve outer part of the balloon. As shown in FIG. 6, FIG. 16, and FIG. 17, the mold 30 may have the distal fourth section 34D and the proximal fourth section 34P, and a fourth groove 49 may be formed on the inner wall surface 36 of at least either one of the distal fourth section 34D and the proximal fourth section 34P. In this case, in the step of allowing the resin to enter the first groove 41, the resin preferably reaches the bottom of the fourth groove 49. Accordingly, a protruding part can also be provided at the position, corresponding to the sleeve outer part of the balloon, in the parison 20.

The depths of the third groove 47 and the fourth groove 49 are preferably smaller than that of the first groove 41. Accordingly, in the step of allowing the resin to enter the first groove 41, the resin is likely to reach the bottom of the third groove 47 or the fourth groove 49 earlier than filling the first groove 41, so that the effect of fixing the position, corresponding to the sleeve part or the sleeve outer part of the balloon, in the parison 20 by the mold 30 can be enhanced. Therefore, when the parison 20 is expanded by introducing a fluid into the lumen 23 of the parison 20, rotation of the parison 20 can be prevented, so that crushing or the like of the protruding part 25 can be prevented.

In the inner cavity cross-section of the mold 30, the shapes of the second groove 45 to the fourth groove 49 may be the same or different from each other. In addition, for the shapes of the second groove 45 to the fourth groove 49, the description of the first groove 41 can be referred to.

This application claims priority based on Japanese Patent Application No. 2019-108432 filed on Jun. 11, 2019, the entire contents of which are incorporated herein by reference.

DESCRIPTION OF REFERENCE SIGNS 1 balloon
2 straight tube part
3 tapered part
4 sleeve part
5 sleeve outer part
6 balloon body
7 outer surface of balloon body
10 protruding part
11 outer end
12 outer surface of protruding part
13 tip end region
14 base end region
A, B, C position
20 parison
21 first end
22 second end
23 lumen
25 protruding part
26 outer end
27 outer surface of protruding part
28 tip end region
29 base end region
30 mold
30A first mold
30B second mold
30C third mold
30D fourth mold
30E fifth mold
30F sixth mold
31 first section
32 second section
32D distal second section
32P proximal second section
33 third section
33D distal third section
33P proximal third section
34 fourth section
34D distal fourth section
34P proximal fourth section
35 inner cavity
36 inner wall surface forming inner cavity
41 first groove
41a bottom
41b part that becomes narrower toward outer side in radial direction
41c part that becomes wider toward outer side in radial direction
41d arc-shaped part
42 contact region
43 non-contact region
45 second groove
47 third groove
49 fourth groove
x1 distal-proximal direction
x2 longitudinal direction of parison
x3 longitudinal direction of mold

The invention claimed is:

1. A method for manufacturing a balloon catheter, comprising:
a step of inserting a tubular parison made of a resin into an inner cavity of a mold having a first groove formed on an inner wall surface forming a part of the inner cavity;
a step of introducing a fluid into a lumen of the parison to inflate the parison such that a part of the parison enters the first groove; and
a step of removing the parison from the mold before the part of the parison reaches a bottom of the first groove, wherein the parison, to be inserted into the inner cavity of the mold, has a protruding part formed on an outer surface of the parison, the protruding part comprising a tip end portion including an end point in a radial direction of the protruding part, and a base portion that is located between the tip end portion and a balloon body, and
the parison is inflated in the cavity of the mold such that the base portion of the protruding part blocks an entrance of the first groove by coming into contact with an inner wall surface of the first groove, and the tip end portion is prevented from being contacting with the inner wall surface of the first groove.

2. The method according to claim 1, wherein a surface roughness of the tip end portion of the protruding part is lower than a surface roughness of the outer surface of the parison measured after the step of allowing the resin to enter the first groove.

3. The method according to claim 1, further comprising a step of polishing an outer surface of the protruding part.

4. The method according to claim 1, further comprising a step of sharpening the protruding part.

5. The method according to claim 1, further comprising a step of roughening an outer surface of the protruding part.

6. The method according to claim 1, wherein the protruding part extends along a longitudinal direction of the parison, and the method further comprises a step of varying a height of the protruding part depending on a position in the longitudinal direction of the parison.

7. The method according to claim 1, wherein the protruding part extends along a longitudinal direction of the parison, and the method further comprises a step of making a cut in an outer surface of the protruding part such that the protruding part is provided with two or more tip ends.

8. The method according to claim 1, wherein the first groove of the mold has a contact region being in contact with the base portion of the parison, and a non-contact region being separated from the tip end portion of the parison; and the contact region has an arc-shaped part formed in an arc shape in a cross-section perpendicular to a longitudinal direction of the mold.

9. The method according to claim 1, wherein the mold has a first section that extends in a longitudinal direction of the mold and that forms a straight tube part of a balloon; and the first groove is formed in the first section.

10. The method according to claim 9, wherein in a longitudinal direction of the mold, the mold has a second section that is located on both sides of the first section and that forms a tapered part of the balloon, and a third section that is located on an end part side in the longitudinal direction of the mold than the second section and that forms a sleeve part of the balloon;

the second section comprises a distal second section located at a position corresponding to a distal side of the balloon than the first section, and a proximal second section located at a position corresponding to a proximal side of the balloon than the first section;

the third section comprises a distal third section that is located at a position corresponding to the distal side of the balloon than the distal second section and that forms a distal sleeve part, and a proximal third section that is located at a position corresponding to the proximal side of the balloon than the proximal second section and that forms a proximal sleeve part;

a third groove shallower than the first groove is formed on an inner wall surface of at least either one of the distal third section and the proximal third section of the mold; and the parison is inflated such that a part of the parison reaches a bottom of the third groove.

11. The method according to claim 10, wherein a parison having a guide part protruding outwardly in a radial direction on an outer surface of the parison is prepared in the step of preparing the parison; and the guide part is placed in the third groove in the step of inserting the parison into the inner cavity of the mold.

12. The method according to claim 9, wherein in a longitudinal direction of the mold, the mold has a second section that is located on both sides of the first section and that forms a tapered part of the balloon, the second section comprises a distal second section located at a position corresponding to a distal side of the balloon than the first section, and a proximal second section located at a position corresponding to a proximal side of the balloon than the first section; and no groove is formed on an inner wall surface of at least either one of the distal second section and the proximal second section of the mold.

13. The method according to claim 1, wherein the first groove has a part that becomes wider toward an outer side in a radial direction.

14. The method according to claim 1, wherein the first groove has a part that becomes narrower toward an outer side in a radial direction.

\* \* \* \* \*